United States Patent
Avinash (10) Patent No.: US 7,512,284 B2
(45) Date of Patent: Mar. 31, 2009

(54) VOLUMETRIC IMAGE ENHANCEMENT SYSTEM AND METHOD

(75) Inventor: Gopal B. Avinash, New Berlin, WI (US)

(73) Assignee: General Electric Company, Schenectady, NY (US)

( * ) Notice: Subject to any disclaimer, the term of this patent is extended or adjusted under 35 U.S.C. 154(b) by 634 days.

(21) Appl. No.: 11/092,487

(22) Filed: Mar. 29, 2005

(65) Prior Publication Data

US 2006/0228036 A1    Oct. 12, 2006

(51) Int. Cl.
*G06K 9/40* (2006.01)

(52) U.S. Cl. ........................ 382/266; 382/260; 382/263

(58) Field of Classification Search .................. 382/131, 382/173, 254, 260, 263, 266, 274, 154
See application file for complete search history.

(56) References Cited

U.S. PATENT DOCUMENTS

| | | | | |
|---|---|---|---|---|
| 5,832,134 A | * | 11/1998 | Avinash et al. | 382/257 |
| 6,592,523 B2 | * | 7/2003 | Avinash et al. | 600/443 |
| 6,701,025 B1 | * | 3/2004 | Avinash | 382/261 |
| 6,754,376 B1 | * | 6/2004 | Turek et al. | 382/131 |
| 6,937,776 B2 | * | 8/2005 | Li et al. | 382/260 |
| 2003/0099405 A1 | * | 5/2003 | Avinash et al. | 382/260 |

* cited by examiner

*Primary Examiner*—Brian Q Le
(74) *Attorney, Agent, or Firm*—Fletcher Yoder (57) ABSTRACT

A technique is described for enhancing three dimensional or volumetric image data, such as thick slice or slab data, or data for slices stacked in a third dimension orthogonal to an imaging plane. The technique processes the image data by reference to data parameters both in two dimensions and in three dimensions. The processing permits identification of structural pixels and their differentiation from non-structural pixels. The structural pixels may be identified by reference to gradients determined in three dimensions, but with directions determined by reference to only two dimensions. The structural and non-structural pixels may then be processed differently to provide an enhanced image.

20 Claims, 6 Drawing Sheets

VOLUMETRIC IMAGE ENHANCEMENT SYSTEM AND METHOD

BACKGROUND

The present invention relates generally to the field of digital imaging and particularly to enhancement of volumetric images. More particularly, the invention relates to techniques for processing images in a combination of two-dimensional and three-dimensional analysis steps.

Digital images are typically made and processed in either two or three dimensions. Two-dimensional (2D) images are conventionally made by impacting a digital detector with radiation. The detector may be a charge coupled device, as in digital cameras, or a more complex detector such as those used in digital X-ray and various radiographic techniques. Three-dimensional (3D) image data may be acquired as a plurality of 2D datasets. Techniques for acquiring 3D images include magnetic resonance imaging (MRI), computer tomography (CT) imaging systems, and so forth.

Techniques have also been developed for enhancing 2D and 3D images. In general, these techniques are specifically adapted to either 2D image enhancement or 3D image enhancement. Assumptions made in either technique may generally hold valid for specific situations only, however. For example, for images having pixels of a first pitch or special resolution (i.e., the number of pixels per unit length or area), in both an image plane and in a third dimension, existing techniques may perform adequately. However, where the dimensions are different, information may be lost or analysis of the content of the images may be distorted. This is particularly true of images having a greater depth in a direction orthogonal to an image plane. Such images may be termed "thick slice" or "thick volumetric" images.

Several 2D and 3D image enhancement frameworks have been proposed for enhancing 2D and 3D images. In general, such enhancement techniques are useful for identifying features and objects of interest, typically visible objects in the images. Depending upon the context, such features may be circumscribed, identified, categorized, and analyzed, such as for recognition purposes. In a medical diagnostic context, for example, various anatomies and disease states may be determined based upon such image analysis. The analysis may similarly be use for visualization of structures and anatomies. In other contexts, such as part inspection, defects and internal features may be visualized and analyzed in a similar manner. Still further, in contexts such as baggage and parcel inspection, the internal contents of objects may be determined by analysis and recognition techniques.

Thick volumetric images have characteristics of both 2D and 3D images. For such images, 2D filtering does not make full use of a third dimension. That is, sampling in a third dimension, which may be referred to as a "Z direction", may be rather poor in such image data, resulting in relatively poor results of the analysis when using 3D filtering.

There is a need, therefore, for improved techniques for analyzing thick volumetric images. There is a particular need for a technique that can make use of additional information provided by volumetric data while still maintaining full use of in-plane data. Such techniques could enhance details by highlighting areas of visual interest better than 2D techniques.

BRIEF DESCRIPTION

The present invention provides novel image enhancement techniques designed to response to such needs. The techniques are particularly well-suited to enhancement of thick volumetric images, that is, images having a sampling along a dimension orthogonal to an imaging plane that is greater than, and particularly over five times that along in-plane dimension. However, the invention is not necessarily limited to any particular thickness, but may be more generally suited to analysis of volumetric images including image data available in two and three dimensions. The technique allows for analysis of fine structures that are sparsely sampled and generally not analyzed or insufficiently analyzed in 3D processing alone. Larger structures are still adequately sampled, however, and can be used for 3D processing in the present technique. The present image filtering framework thus performs analysis via steps in both 2D and 3D processing. The technique may be referred to, therefore, as "2.5D".

The technique may be used in a number of contexts, such as conventional medical imaging, as well as for part inspection and analysis, baggage and parcel inspection and analysis, and so forth. Moreover, the technique is not limited to any particular imaging modality, but may be used with a range of existing modalities. Finally, the technique may be employed directly at an image data acquisition system, or may be used in conjunction with a processing station that may be entirely remote from the image data acquisition system, which may process image data subsequent to image data acquisition, from image data stored in a memory.

In accordance with certain aspects of the techniques, processing steps are performed in reference to 3D image data, while other processing steps are performed in reference to 2D image data. In particular, analysis and segmentation of the structural features in the image data are performed by a combination of 2D and 3D processing. The processing renders a map or binary mask of pixels that are determined to be representative of structure and pixels that are determined to be represented as of non-structure. The image data may then be further processed based upon this categorization.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
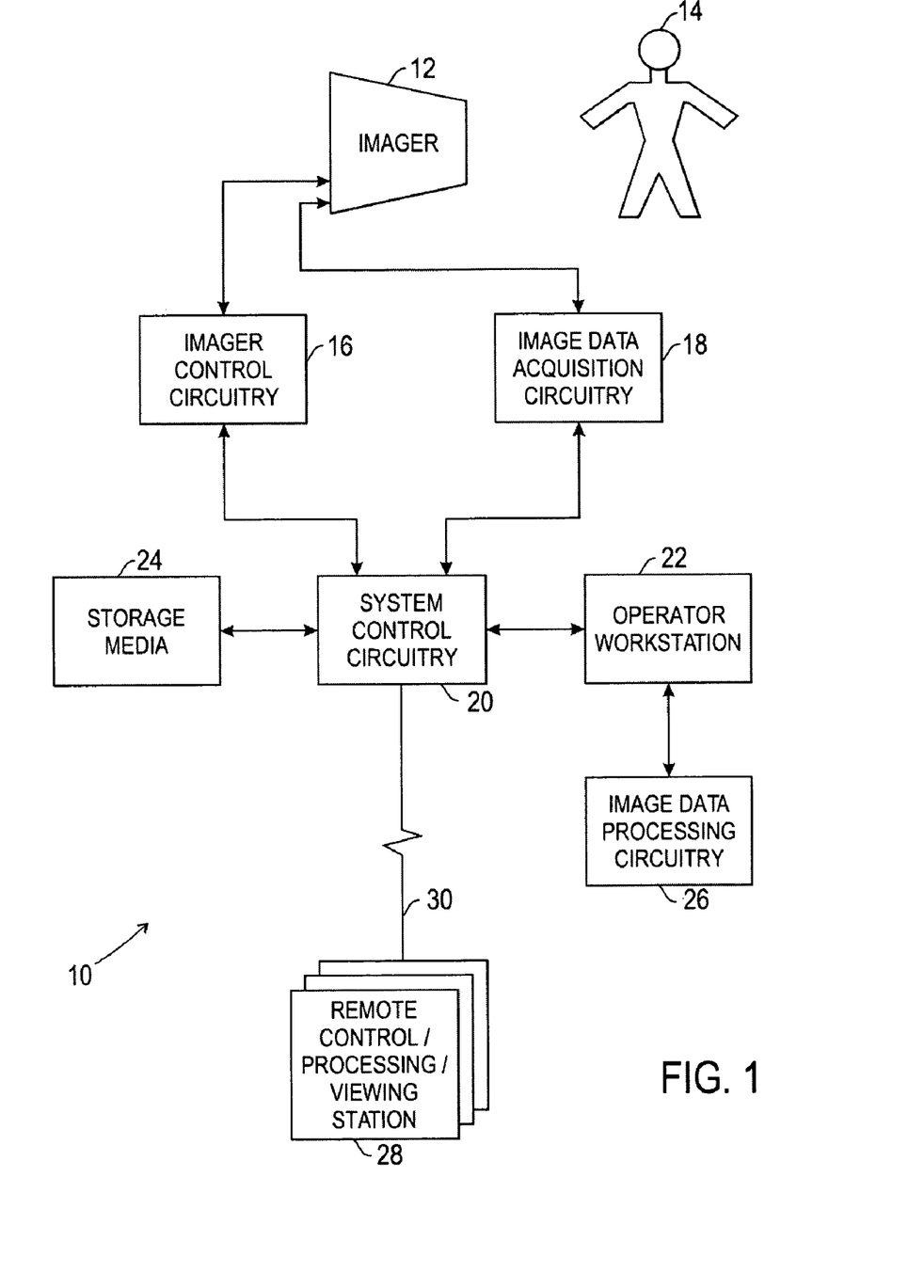
FIG. 1 is a diagrammatical representation of an exemplary imaging system for acquisition of 2D and 3D image data which is processed in accordance with the present technique.

Turning now to the drawings and referring first to FIG. 1, an imaging system 10 is illustrated generally as including an imager 12 for creating image data of a subject 14. Although a human figure is generally shown as the subject 14, it should be borne in mind that any appropriate subject could be imaged. In the present context, for example, the subject may be human or animal, animate or in-animate, such as manufactured parts, naturally occurring subjects and so forth. Indeed, the imaging system 10 may be any suitable type of system that produces digitized image data based upon some imaging physics. In the medical imaging context, as elsewhere, such imaging systems may include MRI systems, PET systems, CT system, tomo-synthesis systems, X-ray systems, ultrasound systems, among many other imaging modalities. The systems may also include conventional photographic imaging systems that produce digitized image data based upon received radiation of any suitable bandwidth or frequency.

In the diagrammatical view of FIG. 1, the imaging system includes an imager 12 coupled to imager control circuitry 16 and image data acquisition circuitry 18. Depending upon the modality and physics of the system, the imager will typically either emit some type of radiation, as with X-ray, CT, tomo-synthesis, and other systems. Other active imaging systems, such as MRI systems, influence subjects by excitation, such as through generation of radio frequency pulses in the presence of controlled magnetic fields. In all these cases, however, the imager is regulated in its operation by the imager control circuitry 16. Such control circuitry may take any suitable form, and typically includes circuitry for activating the imager, receiving radiation or other signals, creating any excitation signals or radiation required for imaging, and so forth. The image acquisition circuitry 18, then, receives and initially processes data received by imager. Such initial processing may include conversion of analog signals to digital signals, filtering of the analog or digital signals, scaling or dynamic range adjustments, and the like.

The image control circuitry 16 and the image data acquisition circuitry 18 are generally regulated by some type of system control circuitry 20. Again, depending upon the nature of the imaging system and the physics involved, the system control circuitry may initiate imaging sequences by exchanging appropriate signals with the imager control circuitry 16. The system control circuitry 20 may also receive the raw or pre-processed image data from the image data acquisition circuitry 18. The system control circuitry 20 may, particularly in more complex systems, be coupled to an operator workstation 22 where an operator selects, configures, and launches examination or imaging sequences. The image data, either raw, partially processed or fully processed, is typically stored in some type of storage media as represented at reference numeral 24. In the present context, such storage media may be part of the system control circuitry 20, the operator workstation 22, or any other component of the overall system. In a medical diagnostics context, for example, such storage media may include local and remote memory, both magnetic and optical, and may include complex picture archive and communication systems (PACS) designed to store and serve image data upon demand.

In the illustration of FIG. 1, the operation workstation 22 is shown as coupled to image data processing circuitry 26. Again, such processing circuitry may actually be distributed throughout the system, and may embody hardware, firmware, and software designed to process the image data to produce reconstructed images for viewing. In accordance with the present techniques described below, the image processing circuitry 26 performs a combination of 2D and 3D ("2.5D") data processing on the image data to manipulate the raw or pre-processed data so as to further enhance the usability of the reconstructed images. The image data processing circuitry 26 may be local to the imaging system, as illustrated generally in FIG. 1, or may be completely remote from the system, and simply access the image data, as from the storage media 24 for post-processing. Finally, FIG. 1 illustrates various remote control/processing/viewing stations 28 that can be coupled to the imaging system by appropriate network links 30. Such stations may be used for further viewing, analyzing, and processing the image data as described herein.

As will be appreciated by those skilled in the art, image data of the type acquired on many different imaging systems is generally processed by various filtering, and enhancement techniques to recognize, clarify, or otherwise manipulate discrete picture elements or pixels that are encoded by the image data. Each pixel typically includes data descriptive of its location and its intensity, or in color systems, its intensity in several different colors. The enhancement of the image data is performed by mathematically computing various characteristics of each pixel and of neighboring pixels so as to recognize and treat the pixels in useful groups. Essentially, the image data is most useful when a human or machine can recognize groups of pixels that share certain qualities or characteristics. For example, structures and non-structures may be recognized in image data by the processes described below. The structures may represent edges, surfaces, contours, regions, colors, and other image features that, when viewed by a human or machine viewer, render the image useful or subject to some type of interpretation.

Figure 2:
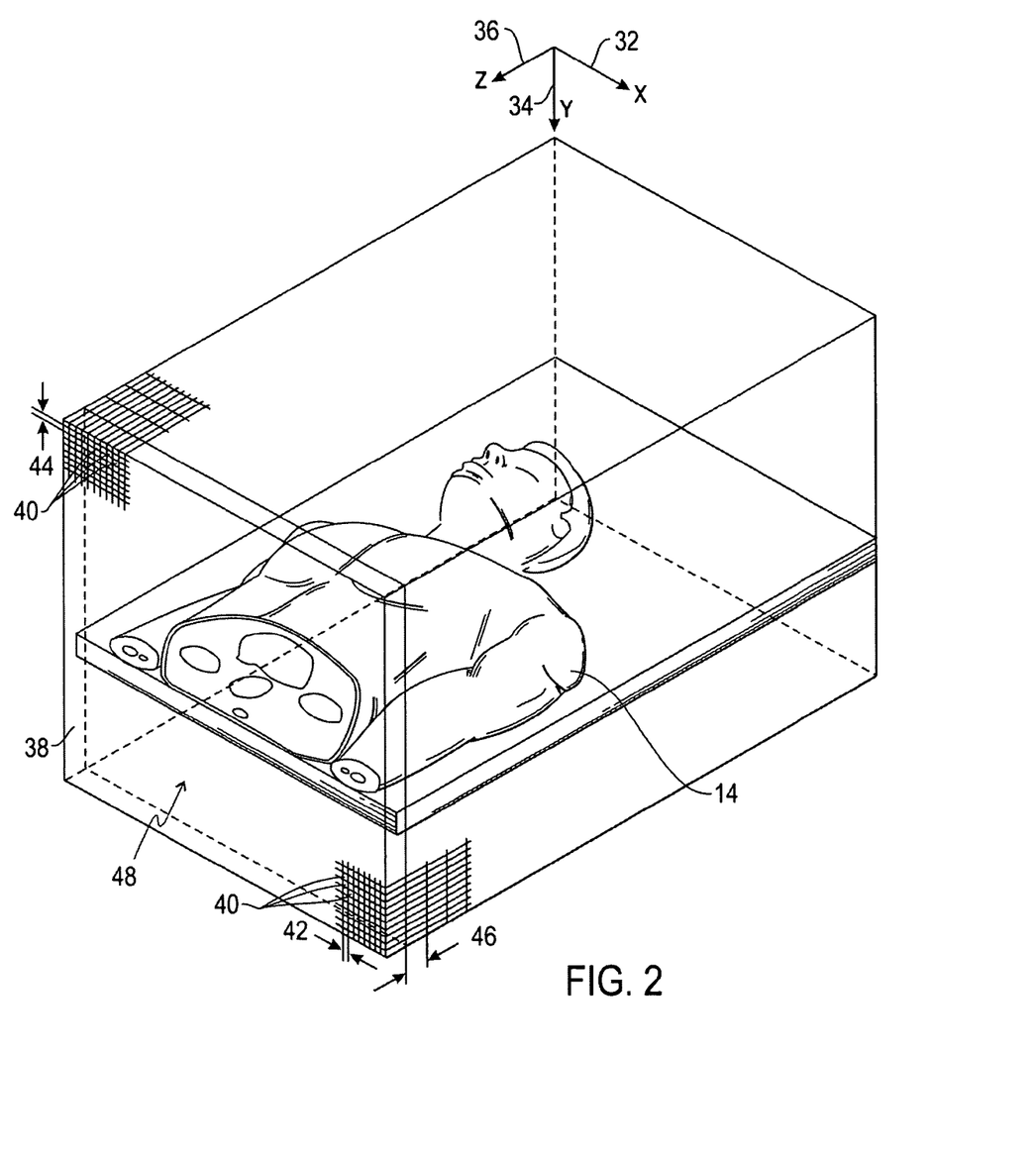
FIG. 2 is an exemplary 3D imaging volume used to make a series of images enhanced by the present technique.

FIG. 2 represents an exemplary imaging volume, such as imaging system 10 described above. As recognized by those skilled in the art, the imaging volume may be analyzed in three orthogonal directions, including an x-direction 32, a y-direction 34 and a z-direction 36. The present 2.5D image enhancement technique or framework enhances thick volumetric images made in the imaging volume by essentially treating such images as 3D objects for analyzing and segmenting purposes to obtain a 3D segmentation mask. However, the framework treats each of the thick slices or images separately for enhancement filtering in 2D while guided by the 3D segmentation mask. As a result, the technique makes use of 3D information for performing 2D filtering. Therefore, the technique has the potential to further improve the robustness of image filtering.

In the illustration of FIG. 2, a slab or slice 38 of the imaging volume is represented as including discrete volume elements (voxels) which are, for the present purposes, referred to as picture elements (pixels) 40 in the selected slap or slice 38. The pixels have a known pitch or dimension in each orthogonal direction, including a pitch 42 in the x-direction, a pitch 44 in y-direction, and a pitch 46 in the z-direction. As will be appreciated by those skilled in the art, a 2D image generally represents the projection of three dimensions into a 2D imaging plane. An image 48 may thus be presented as the projection of the pixels 40 of the slab or slice 38 in an imaging plane at the surface of the slab or slice. As will be appreciated by those skilled in the art, however, where the dimension or pitch 46 in the z-direction differs from that in the x- and y-directions, the projection may not fully render certain of the details that represent features or structures extending back in the z-direction. The image data is processed in the present context in such a manner as to more accurately analyze and process structural features taking such detail into account.

Figure 3:
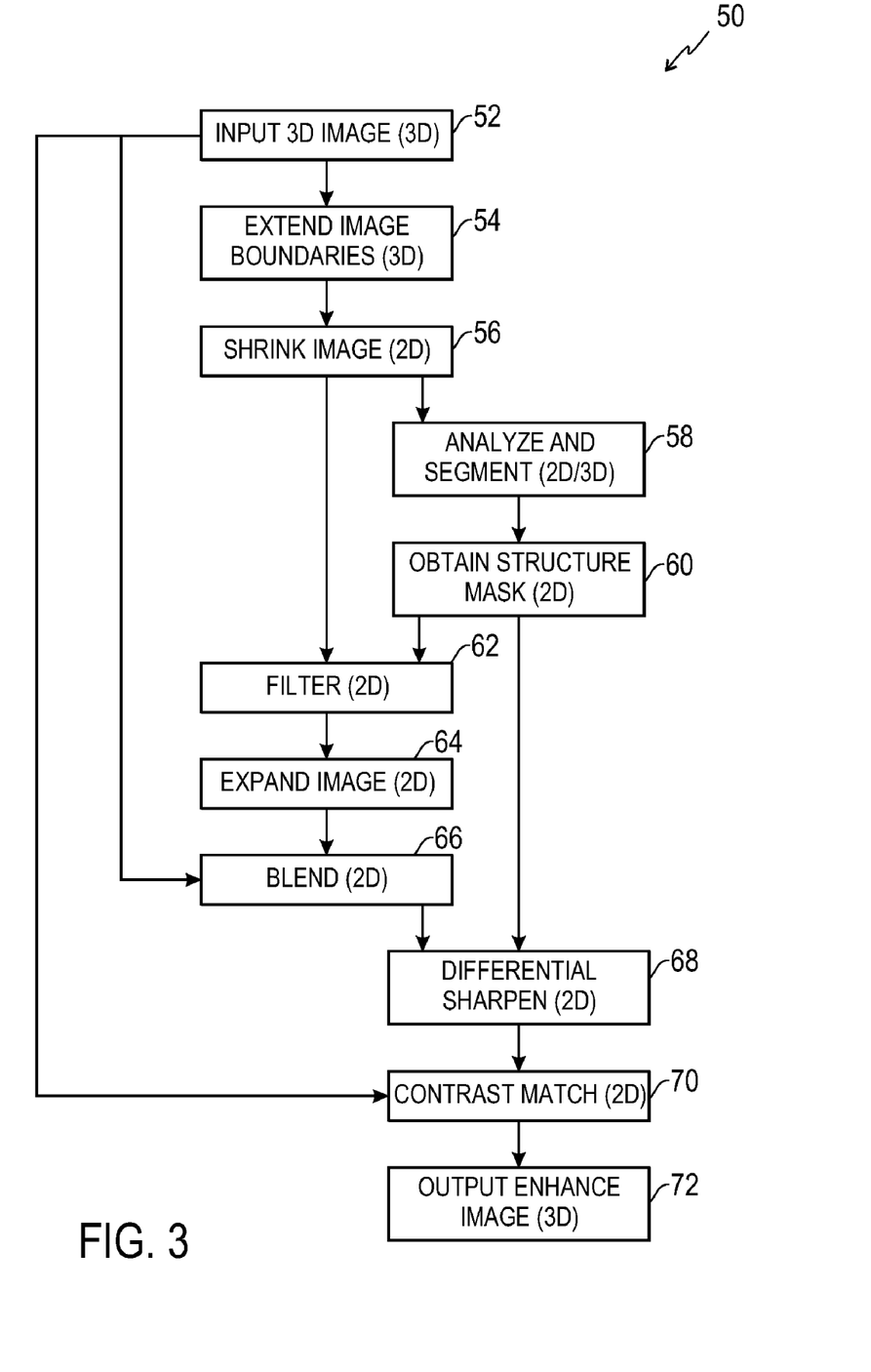
FIG. 3 is a diagrammatical representation of exemplary logic for carrying out the 2.5D image enhancement scheme of the present technique.

Exemplary logic for carrying out certain of the image enhancement steps according to the present technique is illustrated in FIG. 3 and designated generally by the reference numeral 50. The processing logic begins with the input or access to 3D image data as indicated at step 52. As will be appreciated by those skilled in the art, the image data typically includes a series of values, digitized over a useful dynamic range. Each pixel in the image data corresponds to one of the image data values. The image data itself may be included in a larger image data stream, which may include such other features as descriptive headers, identification data, date tags, compression routine identifiers, and so forth. In the present context, the image data includes a pixel data which may be referred to as $I_1(x,y,z)$, where the term "$I_1$" represents the collective values of each pixel in the image at individual locations defined by the parenthetical.

At step 54, boundaries of the image are extended by mirroring. As will be appreciated by those skilled in the art, such mirroring permits analysis and computations to be made on pixel data near boundaries of the image, particularly where spatial filters are employed as described below. In the present context, the mirroring is performed by adding pixels to each side of the 3D image with a first added pixel adjacent to each image pixel being equal in value to the image pixel itself, and a second adjacent at a pixel being equal to the pixel value of the immediately adjacent pixel in the image data. Such mirroring may be done for any suitable number of rows or columns of the image data. In a present implementation, a kernel having dimensions of 3×3 is employed as described below, such that mirroring is performed by adding two rows or columns or slices in each of the three image dimensions.

At step 56, the image is shrunk to facilitate analysis. The shrinking is performed by replacing each pixel with the average value of neighboring pixels. The number of pixels considered for averaging may depend upon a shrink factor which may be programmed into the present algorithm, or may be selected by a user. In a present implementation, shrinking is performed two dimensionally for each slice of the image data. Those still in art will also recognize that the mirroring performed at step 54 facilitates computation of the pixel average values for those pixels near the image boundaries. The resulting shrunk image data is referred to as $I_2(x,y,z)$.

At step 58 in FIG. 3, analysis and segmentation are performed on the shrunk image $I_2(x,y,z)$. The analysis and segmentation are intended to generate a mask or map of structural pixels and non-structural pixels. That is, pixels considered to be representative of features of interest in the image, typically edges and more prominently contrasting details, may be termed "structural." While other features, including texture, may not be considered structural, they may nevertheless be important for overall image analysis, visualization, and so forth. However, processing of structural pixels differently from non-structural pixels has been found to be particularly useful in developing enhanced images. Before proceeding to the other steps summarized in FIG. 3, the detailed steps involved in the analysis and segmentation performed at step 58 are described with particular reference to FIG. 6.

Figure 4:
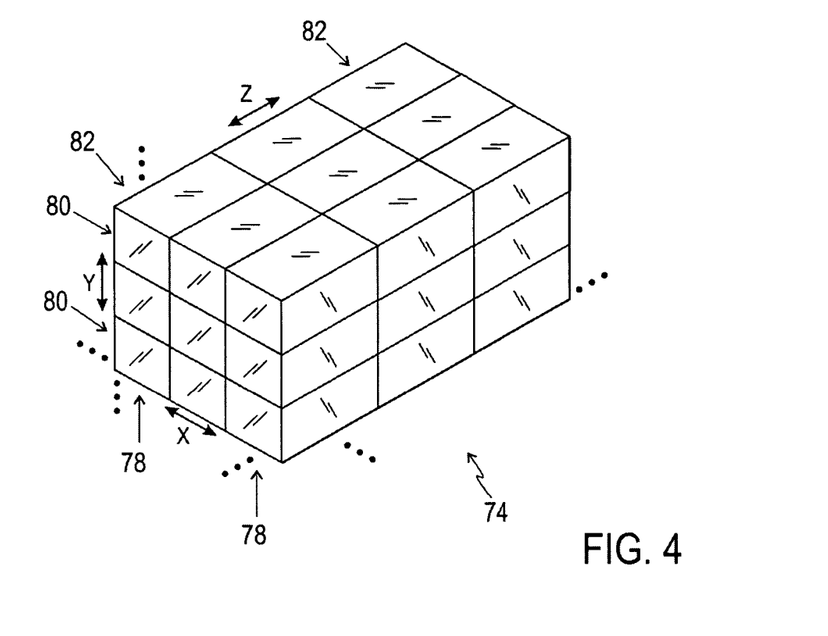
FIG. 4 is a perspective view of an exemplary portion of an imaging volume used to illustrate how a block or neighborhood of pixel data is employed in the analysis of FIG. 3.
Figure 5:
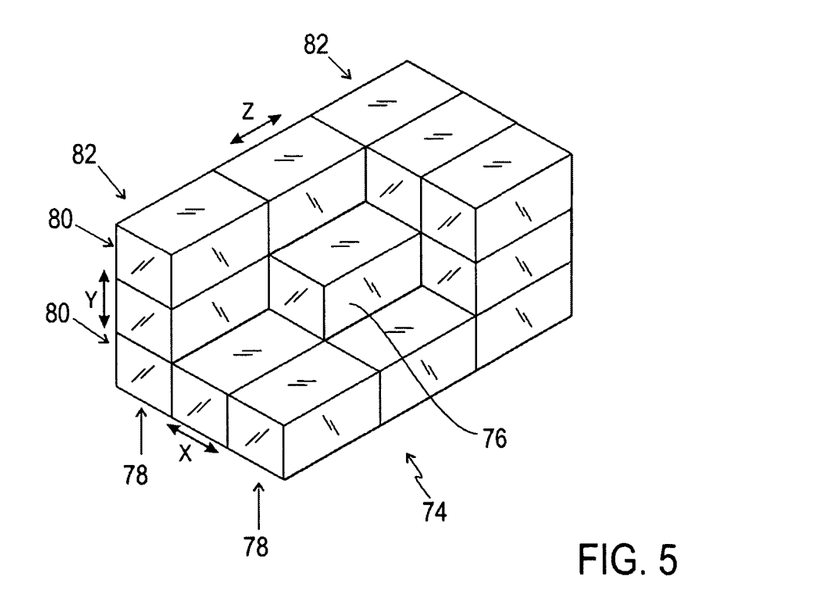
FIG. 5 is a similar perspective view with certain neighboring pixels removed to permit viewing of an internal pixel of interest.
Figure 6:
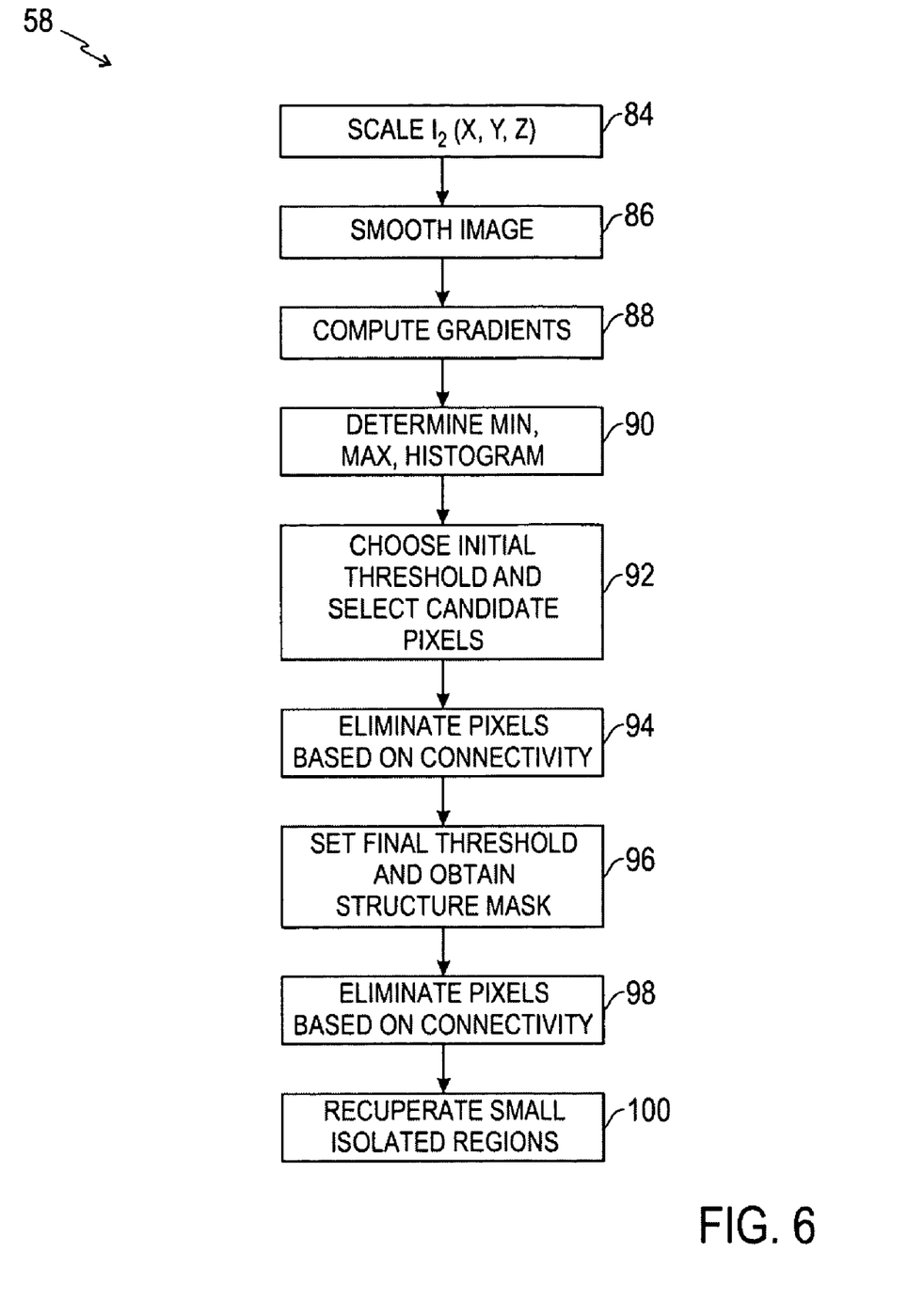
FIG. 6 is a diagrammatical representation of exemplary steps in logic for the analysis and segmentation summarized in FIG. 3.

The analysis summarized in FIG. 6 makes use of pixel neighborhoods that may be visualized as illustrated in FIGS. 4 and 5. In particular, the pixels of an individual image or slice of the imaging volume may generally fall within one plane, such as the middle vertical plane of pixels shown in FIGS. 4 and 5. The volume portion 74, then, consists of this plane of pixels and additional pixels on either side of the plane. FIG. 5 illustrates the volume portion 74 with certain pixels removed to show a center pixel 76 which, in the analysis described below, may be any pixel in the image, and is referred to as the pixel of interest. The pixel of interest 76, then, may include as many as 26 neighboring pixels. That is, pixels 78 neighbor the center pixel 76 in an x-direction, pixels 80 neighbor the center pixel 76 in a y-direction, and pixels 82 neighbor the center pixel 76 in a z-direction. Throughout the present discussion, reference will be made to this neighborhood as a 3×3 neighborhood, although larger neighborhoods may be employed for the processing.

Referring now to FIG. 6, exemplary steps in the analysis and segmentation illustrated in FIG. 3 are presented. In the illustrated analysis, the shrunk image $I_2(x,y,z)$ is first scaled. This scaling is performed by identifying maximum and minimum values for all pixels in the image, referred to in a present implementation as "maxorig" and "minorig," respectively. In a present implementation, a scale factor is determined by dividing a dynamic range value by the value of maxorig, with a present dynamic range value equally 4095. Other values may, of course, be employed. The scaled value of each pixel, then, is computed by subtracting the value of minorig from each individual pixel value, and multiplying the resulting difference by the scale factor.

The scaled image is then smoothed as indicated at step 86 in FIG. 6. In a present implementation, this smoothing is performed via a 3D boxcar filter wherein each pixel becomes the center pixel or pixel of interest as illustrated in FIGS. 4 and 5 above, and each pixel value is sequentially replaced by the average value of all pixels in the 3×3×3 neighborhood. The smoothing is performed based upon the values of pixels in the image $I_2(x,y,z)$.

Figure 7:
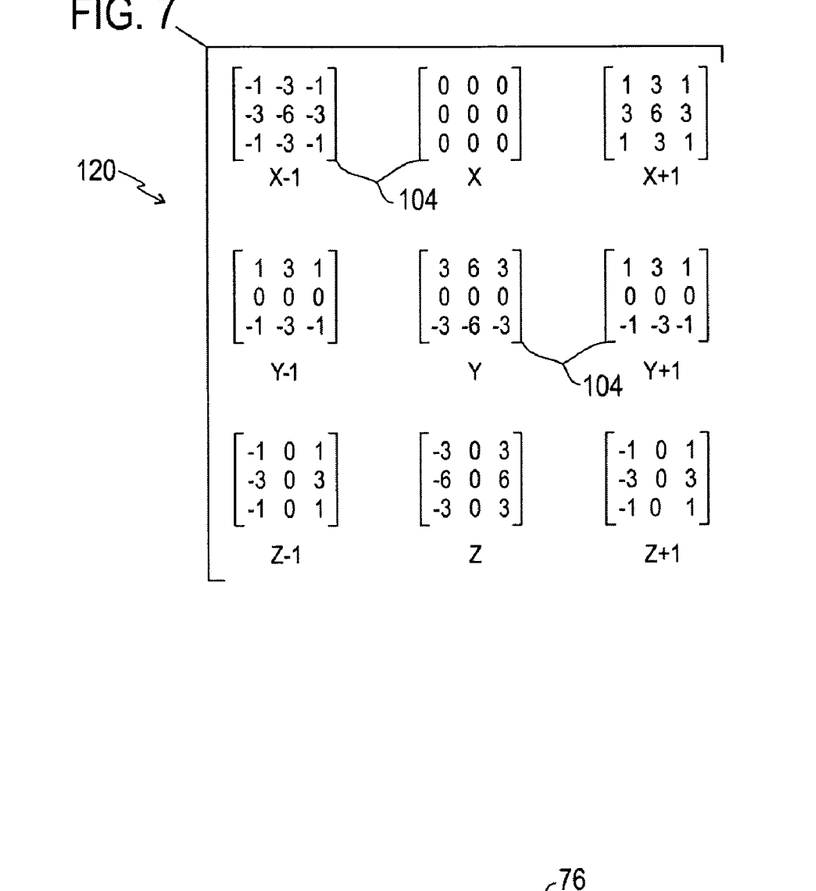
FIG. 7 is a depiction of a series of matrix operators employed for the analysis of FIG. 6.

At step 88, the output of the boxcar filter is used to calculate gradients for each pixel. As will be appreciated by those skilled in the art, in the digital imaging context, a "gradient" represents a difference between the value of a pixel of interest and a value of one or more additional (i.e., neighboring) pixels. In step 88, multiple gradients are calculated for components in x, y and z directions. The components in the X, Y and Z directions called in a present implementation "gradX," "gradY" and "gradZ" are calculated using the Sobel 3D gradient operators set forth in FIG. 7. As those skilled in the art will recognize, the Sobel operators 102 are defined by a series of matrices 104 which may be multiplied by pixels at various locations in the 3×3×3 neighborhood to obtain the component values. Based upon these component values, then, a gradient magnitude for the pixel of interest may be calculated in 3D in accordance with the relationship:

gradient magnitude=sqrt($gradX^2+gradY^2+gradZ^2$)

While the gradient magnitude is computed in reference to the 3D components, however, its direction is computed in reference to only two dimensions, those defining the image plane or projection. In the present context, the direction is computed in accordance with the relationship:

direction=arctan (gradY/gradX).

Once the gradient magnitudes and directions have been computed for each pixel in the shrunken image, the maximum and minimum gradients are determined, and a gradient histogram is obtained as indicated at step 90 in FIG. 6. The maximum minimum gradients are determined by reference to the gradient magnitudes. As will be appreciated by those skilled in the art, the gradient histogram, then, defines the number or counts of individual pixels having particular gradients magnitudes. In a present implementation, the histogram includes gradients for all voxels, each voxel having one gradient magnitude associated with it. Maximums and minimums are computed over each gradient value of all voxels. The histogram may be represented as a bar graph with gradient magnitudes along a horizontal axis and counts or number of pixels having each individual gradient magnitude along a vertical axis. In practice, however, the processor simply stores addresses of pixels, their gradient values, and the counts for each magnitude.

At step 92, an initial threshold value is chosen and candidate structural pixels are selected. The threshold value employed at this step is an initial gradient threshold value which is chosen initially at a value such that the gradient magnitude of 30% of the pixels in the image $I_2(x,y,z)$ will lie below the threshold. All pixels having values that lie above the initial gradient threshold are then counted. In a present implementation, a directional criteria is also imposed. That is, for a pixel to be counted as a candidate structural pixel, the gradient magnitude of the pixel must lie above the initial gradient threshold, and the gradient direction of the pixel must be above a particular angle, termed "gradangle" in a present implementation. If the count is above a predetermined value or count number, the pixel is retained as a possible relevant edge. The collection of relevant edge pixels is then noted, such as in a mask or map wherein candidate structural pixels have a value of "1" and candidate non-structural pixels have a value of "0".

At step 94 in FIG. 6, certain pixels of the mask are eliminated based upon connectivity. In this process, each pixel having a value of 1 in the binary mask is assigned an index number beginning with the upper-left hand corner of the image and proceeding to the lower right. The index numbers are incremented for each pixel having a value of 1 in the mask. The mask is then analyzed row-by-row beginning in the upper left by comparing the index values of pixels within small neighborhoods. For example, when a pixel is identified having an index number, a four-connected comparison is carried out, wherein the index number of the pixel of interest is compared to index numbers, if any, for pixels immediately above, below, to the left, and to the right of the pixel of interest. The index numbers for each of the connected pixels are then changed to the lowest index number in the connected neighborhood. The search, comparison and reassignment then continues through the entire pixel matrix, resulting in regions of neighboring pixels being assigned common index numbers. In the preferred embodiment the index number merging may be executed several times. Each subsequent iteration is preferably performed in an opposite direction (i.e., from top-to-bottom, and from bottom-to-top).

Following the iterations accomplished through subsequent search and merger of index numbers, the index number pixel matrix will contain contiguous regions of pixels having common index numbers. A histogram is then generated from this index matrix by counting the number of pixels having each index number appearing in the index matrix. As will be apparent to those skilled in the art, each separate contiguous region of pixels having index numbers will have a unique index number. Regions represented by index numbers having populations lower than a desired threshold are eliminated from the definition of structure. In a presently preferred embodiment, regions having a pixel count lower than 50 pixels are eliminated. The number of pixels to be eliminated in this step, however, may be selected as a function of the matrix size, and the amount and size of isolated artifacts to be permitted in the definition of structure in the final image.

At step 96, a final threshold is set for structural pixels and the structure mask is refined based upon this threshold. Again, the structure mask or map will generally correspond to a listing of the pixels in the image $I_2(x,y,z)$ that are considered representative of structures in the image. Again, each pixel may be represented in the structure mask as a "1" or a "0" such that the structure mask, wherein the value "1" represents that the individual pixel is determined to represent structure. The final gradient threshold set at step 96 for determination of the structure mask includes the addition of a desired number of pixels to the number labeled as "1" in the mask (the binary mask count). For example, in a presently preferred embodiment a value of 4,000 is added to the binary mask count to arrive at a desired number of pixels in the image structure definition. This parameter may be set as a default value, or may be modified by an operator. In general, a higher additive value produces a sharper image, while a lower additive value produces a smoother image. This parameter, referred to in the present embodiment as the "focus parameter" may thus be varied to redefine the classification of pixels into structures and non-structures.

The final gradient threshold or FGT is then determined. In particular, the population counts for each gradient magnitude value beginning with the largest magnitudes are summed moving toward the lowest magnitudes. Once the desired number of structural pixels is reached (i.e., the number of pixels counted plus the focus parameter), the corresponding gradient magnitude value is identified as the final gradient threshold. In the presently preferred embodiment, the FGT value is then scaled by multiplication by a value which may be automatically determined or which may be set by a user. For example, a value of 1.9 may be employed for scaling the FGT, depending upon the image characteristics, the type and features of the structure viewable in the image, and so forth. The use of a scalable threshold value also enables the technique to be adapted easily and quickly to various types of images, such as for MRI data generated in systems with different field strengths, CT data, and so forth.

Figure 8:
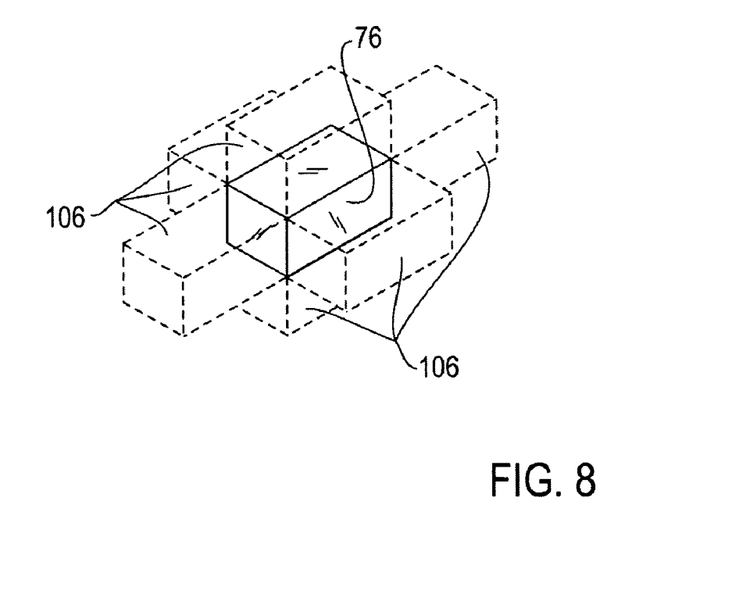
FIG. 8 is perspective view of a reduced neighborhood set for certain of the analysis performed in accordance with the steps of FIG. 6.

At step 98, pixels are eliminated based upon connectivity. In the present implementation, pixels are eliminated at this step if the individual pixel has less than a defined threshold count from the mask using a 6-connectivity approach. That is, each pixel is considered a central pixel in a reduced neighborhood, with only pixels bordering the pixel of interest at a face are considered. FIG. 8 represents such a reduced neighborhood in which a pixel of interest or central pixel 76 is shown and the reduced neighborhood of pixels at its faces are designated by reference numeral 106. Considering such a reduced neighborhood, pixels are eliminated by a process otherwise identical to that described above with reference to step 94.

At step 100, small or isolated regions or volumes of pixels may be recuperated or included in the collection of pixels determined to be potential structures, to provide continuity of edges and structures. In this process, a threshold is determined that may be referred to as a follower ratio, as a percentage of the final gradient threshold. If a pixel is above the follower ratio, and is connected to the pixels which are above the final gradient threshold (i.e., candidate structural pixels), then the corresponding binary value of the pixel is changed. Such gradient following is generally carried out recursively in all three dimensions, resulting in an initial classification of the pixels as structural or non-structural.

Based upon such determinations, processing continues as indicated at step 60 in FIG. 3. That is, once the analysis and segmentation of the individual pixels are made based upon the 2.5D approach, a structure mask is obtained at step 60. This structure mask is obtained by repeating the process of obtaining a final binary mask that describes structural and non-structural regions of each projection image in the imaging volume. The final binary mask is obtained by comparing the pixel count with a preset threshold, termed in a present implementation as "countthreshold1". That is, if a current pixel has a binary mask value of 1, the neighborhood pixel count is computed. If the pixel count is above the threshold, the current pixel value in the mask is set to 1. Otherwise it is set to 0. If the current pixel value is 0 in the mask, the same account is computed and if it is above a lower threshold, termed in a present implementation "countthreshold2", the binary value for the pixel in the mask is set to 1. Otherwise it is set to 0. The resulting map of binary values represents the determinations of the pixels representing structure (those having a value of 1), and those representing non-structure (those having a value of 0).

At step 62 in FIG. 3, the shrunk image $I_2(x,y,z)$ is filtered. In a present implementation, three types of filtering are performed on the image data, including orientation smoothing, homogenization smoothing and orientation sharpening. It should be noted that this filtering is performed based upon the structure mask determined at step 60. That is, although the filtering is performed in two dimensions, whether the filtering is performed and how the filtering is performed is based upon the structure as determined by reference to two and three dimensional analysis.

In the orientation smoothing that may be performed at step 62, the value of certain pixels is replaced with a value that is the average of itself and those of neighboring pixels. In particular, depending upon whether dominant orientation smoothing or local orientation smoothing is desired, processing is as follows. If dominant orientation smoothing is selected, smoothing begins with assigning directional indices to each pixel identified as a structural pixel. In the present embodiment, one of four directional indices is assigned to each structural pixel in accordance with the statistical variances for each pixel. Within a local neighborhood surrounding each structural pixel, statistical variances for pixel kernels in four directions are computed by reference to the normalized intensity values of the surrounding pixels. The direction of the minimum variance is selected from the four computed values and a corresponding directional index is assigned. In the present embodiment these directional indices are assigned as follows: "1" for 45 degrees; "2" for 135 degrees; "3" for 90 degrees; and "4" for 0 degrees. A local area threshold value is assigned based upon the image matrix size. In the present embodiment, a local area threshold of 6 is used for 256×256 pixel images, a value of 14.25 is used for 512×512 pixel images, and a value of 23 is used for 1024×1024 pixel images. A dominant orientation is established for each structural pixel by examining the directional indices within a local neighborhood surrounding each structural pixel. In this process, the directional indices found in the local neighborhood are counted and the pixel of interest is assigned the directional index obtaining the greatest count (or the lowest index located in the case of equal counts).

In the present embodiment, both the dominant direction and its orthogonal direction are considered to make a consistency decision in the dominant orientation smoothing operation. These directions are 1 and 2, or 3 and 4. It has been found that considering such factors substantially improves the robustness of the dominant orientation determination in the sense of being consistent with the human visual system (i.e. providing reconstructed images which are intuitively satisfactory for the viewer).

The consistency decision this made may be based upon a number of criteria. In the present embodiment, the image is smoothed along the dominant direction (i.e., the direction obtaining the greatest number of counts in the neighborhood) if any one of the following criteria is met: (1) the number of counts of the orientation obtaining the greatest number is greater than a percentage (e.g., 67%) of the total neighborhood counts, and the orthogonal orientation obtains the least counts; (2) the number of counts of the orientation obtaining the maximum counts is greater than a smaller percentage than in criterion (1) (e.g., 44%) of the total neighborhood counts, and the orthogonal direction obtains the minimum number, and the ratio of the counts of the dominant direction and its orthogonal is greater than a specified scalar (e.g., 5); or (3) the ratio of the dominant direction counts to its orthogonal direction counts is greater than a desired scalar multiple (e.g., 10).

In the present embodiment, the neighborhood size used to identify the direction of dominant orientation is different for the series of image matrix dimensions considered. In particular, a 3×3 neighborhood is used for 256×256 pixel images, a 5×5 neighborhood is used for 512×512 pixel images, and a 9×9 neighborhood is used for 1024×1024 pixel images.

Subsequently, the count determined in the searched neighborhood for each pixel is compared to the local area threshold. If the count is found to exceed the local area threshold, the intensity value for each structural pixel is set equal to the average intensity of a 1×3 kernel of pixels in the dominant direction for the pixel of interest. Subsequently, the value of a corresponding location in the binary matrix structure map changed from 0 to 1. If the count is found not to exceed the local area threshold for a particular pixel, the intensity value for the pixel of interest is set equal to a weighted average determined by the relationship:

$$\text{weighted avg} = (1/(1+p))(\text{input}) + (p/(1+p))(\text{smoothed value});$$

where the input value is the value for the pixel of interest at the beginning of smoothing, p is a weighting factor between 1 and 200, and the smoothed value is the average intensity of a 1×3 kernel in the dominant direction of the pixel of interest.

Subsequently, the values of each pixel in the binary structure mask are evaluated. If the value is found to equal zero, the corresponding intensity value is multiplied by a weighting factor $\alpha$. In the present embodiment, factor $\alpha$ is set equal to 0.45. The resulting value is summed with the product of the normalized intensity value for the corresponding pixel and a weighting factor $\beta$. In the present embodiment, the factors $\alpha$ and $\oplus$ have a sum equal to unity, resulting in a value of $\beta$ equal to 0.55.

If the value for a particular pixel is found to equal 1 in the binary structure mask, the processor determines whether the desired number of iterations have been completed, and if not, returns to further smooth the structural regions. In the present embodiment, the operator may select from 1 to 10 such iterations.

Homogenization smoothing is performed on non-structure pixels. In one implementation, the homogenization smoothing iteratively averages each non-structural pixel based upon a 3×3 kernel.

Orientation sharpening is performed on the orientation filtered or smoothed structural pixels. Orientation sharpening is performed for those pixels having gradients above a pre-specified limit, such as twice a final gradient threshold used for determining the structural pixels.

Following the filtering operations, processing may include renormalizing the pixels. Such renormalization is performed by computing the average pixel intensity in the filtered image $I_1(x,y,z)$ and obtaining a normalizing factor based thereon. In accordance with a present implementation, the normalizing factor may be computed for each pixel by dividing the mean value before filtering by the mean value after filtering. The normalized image, then, is obtained by multiplying each pixel value in the original image $I_1(x,y,z)$ by the normalization factor, and then adding the minimum value minorig.

The filtered and renormalized image values, then, are expanded to bring the filtered image back to its original size. This step, summarized at reference numeral 64 in FIG. 3 essentially reverses the shrinking performed at step 56. As will be appreciated by those skilled in the art, such expansion may be performed by bi-cubic or bilinear interpolation. The image expansion is performed two dimensionally.

At step 66 texture blending is performed to recapture certain of the texture present in the original data. In the present implementation, the renormalized expanded image is blended on a pixel-by-pixel basis with the pre-filtered image. The amount of original blending with the filtered image can be varied and the blending is performed based upon relationship:

$$I(x,y,z)=\text{blend}*(I(x,y,z)-A(x,y,z))+A(x,y,z);$$

where I(x,y,z) is the renormalized filtered and expanded image, "blend" is a blending parameter, A(x,y,z) is the pre-filtered image.

At step 68, the sharpening is referred to as differential because different amounts of sharpening are performed on structural pixels versus non-structural pixels, by reference again to the structure mask obtained at step 60. Contrast or intensity matching is performed, based upon the original image data. That is, the sharpened image and the original image are both filtered using a low pass (e.g., boxcar) filter and the intensity matching is brought about using the relationship:

$$I(x,y,z)=I(x,y,z)*[\text{lowpassfiltered}(I(x,y,z))/\text{lowpassfiltered}(A(x,y,z))];$$

where the images I(x,y,z) and A(x,y,z) as are described above.

As noted above, following the foregoing processing, the resulting image data may be displayed, stored, and transmitted for viewing. Moreover, more than one image in the image volume may be similarly enhanced, and a collection of images stored for viewing and analysis. The foregoing techniques provide improved processing in all such contexts, particularly where a size or sampling rate of pixels or voxels is substantially greater in one dimension than in others.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for enhancing a discrete pixel image comprising:
   using a processor to perform the steps of:
      identifying structural and non-structural pixels in image data by analysis of the image data in two and three dimensions; and
      further processing the image data in two dimensions based upon the identification of structural and non-structural pixels, wherein the structural pixels are identified by reference to gradient magnitude values computed from three-dimensional data and gradient direction values computed from two-dimensional data.

2. The method of claim 1, wherein the structural pixels are identified based upon a combination of criteria including three-dimensional gradient magnitude values and two dimensional gradient direction values.

3. The method of claim 2, wherein the structural pixels are identified as pixels having a gradient magnitude above a desired threshold and a gradient angle above a desired angle.

4. The method of claim 1, wherein identifying structural and non-structural pixels is based upon analysis pixels neighboring each pixel in three dimensions.

5. The method of claim 1, wherein a structure mask is generated for pixels identified as structural pixels.

6. The method of claim 1, wherein the image data encodes pixels having a first pitch in two dimensions of an image plane and a third pitch greater than the first pitch in a third dimension orthogonal to the image plane.

7. The method of claim 1, wherein the further processing includes filtering of the image data in two dimensions by reference to the identified structural and non-structural pixels.

8. The method of claim 7, wherein the filtering includes orientation smoothing, homogenization smoothing and orientation sharpening.

9. The method of claim 1, wherein the further processing includes blending from original image data into processed image data.

10. The method of claim 1, wherein structural pixels are distinguished from non-structural pixels based upon three-dimensionally smoothed original image data.

11. A method for enhancing a discrete pixel image comprising:
    using a processor to perform the steps of:
       identifying structural and non-structural pixels in image data by reference to gradient magnitude values computed from three-dimensional data and gradient direction values computed from two dimensional data; and
       further processing the image data in two dimensions based upon the identification of structural and non-structural pixels.

12. The method of claim 11, wherein the gradient magnitude and direction values are computed based upon three-dimensionally smoothed image data.

13. The method of claim 11, wherein the structural pixels are identified based upon a combination of criteria including three-dimensional gradient magnitude values and two dimensional gradient direction values.

14. The method of claim 13, wherein the structural pixels are identified as pixels having a gradient magnitude above a desired threshold and a gradient angle above a desired angle.

15. A system for enhancing a discrete pixel image comprising:
    a memory circuit for storing discrete pixel image data; and
    a processing circuit for identifying structural and non-structural pixels in image data by analysis of the image data in two and three dimensions, and for further processing the image data in two dimensions based upon the identification of structural and non-structural pixels, wherein the structural pixels are identified by reference to gradient magnitude values computed from three-dimensional data and gradient direction values computed from two-dimensional data.

16. The system of claim 15, further comprising an image data acquisition system for generating the discrete pixel image data of a subject of interest.

17. The system of claim 16, wherein the image data acquisition system is a computed tomography imaging system.

18. The system of claim 15, wherein the memory circuit is remote from the processing circuit.

19. A device comprising:
    at least one computer-readable medium; and
    computer readable code stored on the at least one computer-readable medium including instructions for identifying structural and non-structural pixels in image data by analysis of the image data in two and three dimensions, and for further processing the image data in two dimensions based upon the identification of structural and non-structural pixels, wherein the structural pixels are identified by reference to gradient magnitude values computed from three-dimensional data and gradient direction values computed from two-dimensional data.

20. A device comprising:

at least one computer-readable medium; and
computer readable code stored on the at least one computer-readable medium including instructions for identifying structural and non-structural pixels in image data by reference to gradient magnitude values computed from three-dimensional data and gradient direction values computed from two dimensional data, and for further processing the image data in two dimensions based upon the identification of structural and non-structural pixels.

* * * * *